United States Patent [19]
Pathak et al.

[11] Patent Number: 6,113,944
[45] Date of Patent: Sep. 5, 2000

[54] PAROXETINE TABLETS AND PROCESS TO PREPARE THEM

[75] Inventors: Ram Dutta Pathak, Epsom Downs; David George Doughty, Welwyn Garden City, both of United Kingdom

[73] Assignee: SmithKline Beecham p.l.c., Brentford, United Kingdom

[21] Appl. No.: 09/108,138

[22] Filed: Jun. 30, 1998

Related U.S. Application Data

[62] Division of application No. 08/676,331, filed as application No. PCT/EP94/04164, Dec. 14, 1994, abandoned.

[30] Foreign Application Priority Data

Dec. 15, 1993 [GB] United Kingdom ............... 9325644

[51] Int. Cl.⁷ .................................................. A61K 9/20
[52] U.S. Cl. ........................... 424/464; 424/489; 424/465
[58] Field of Search ................................... 424/464, 465, 424/489; 514/418

[56] References Cited

U.S. PATENT DOCUMENTS

| | | |
|---|---|---|
| 4,009,196 | 2/1977 | Kurozumi et al. . |
| 4,721,723 | 1/1988 | Barnes et al. . |
| 4,861,893 | 8/1989 | Barrett . |
| 4,902,801 | 2/1990 | Faruk et al. . |
| 5,039,803 | 8/1991 | Smith et al. . |
| 5,776,969 | 7/1998 | James ...................................... 514/418 |

FOREIGN PATENT DOCUMENTS

| | | |
|---|---|---|
| 0 188 081 | of 1986 | European Pat. Off. . |
| 223 403 | of 1987 | European Pat. Off. . |
| 0269 303 | of 1988 | European Pat. Off. . |
| WO92/09281 | of 1992 | WIPO . |
| WO93/22284 | of 1993 | WIPO . |

OTHER PUBLICATIONS

FDA FOIA Materials, Jun. 1993.

*Primary Examiner*—Thurman K. Page
*Assistant Examiner*—William E. Benston, Jr.
*Attorney, Agent, or Firm*—Wayne J. Dustman; William T. King; Charles M. Kinzig

[57] ABSTRACT

Invented is a novel pharmaceutical composition containing Paroxetine.

1 Claim, No Drawings

PAROXETINE TABLETS AND PROCESS TO PREPARE THEM

This is a divisional of application Ser. No. 08/676,331 filed Jun. 12, 1996, abandoned which is a §371 of PCT/EP94/04164, filed Dec. 14, 1994.

The present invention relates to novel formulations and to the use of the formulation in the treatment and/or prevention of certain disorders.

U.S. Pat. 4,007,196 describes certain compounds which possess anti-depressant activity. One specific compound mentioned in this patent is known as paroxetine and which has the following formula:

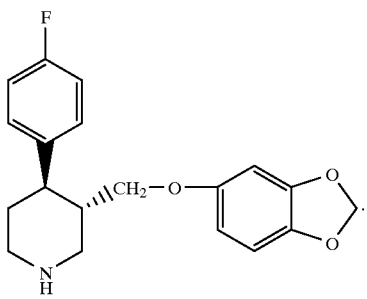

This compound has been approved for human use and is being sold in many countries around the world as an anti-depressant agent.

It has been noticed that tablets of paroxetine often develop a pink hue which is highly undesirable.

To date, all tablets which have been sold have been formulated using an aqueous granulation process. It has surprisingly been found that formulation of paroxetine into tablets can be carried out reliably and on a commercial scale using a formulation process in which water is absent, such as by direct compression or by dry granulation.

It has also been surprisingly found that paroxetine formulated into a tablet using a process in which water is absent, is much less likely to develop a pink hue.

Accordingly, the present invention provides paroxetine which is formulated into tablets using a formulation process in which water is absent.

Examples of such a formulation process are dry direct compression of paroxetine or dry granulation of paroxetine followed by compression into tablets. The present invention therefore provides a formulation comprising direct compressed paroxetine admixed with dry excipients in the form of a tablet and a formulation comprising dry granulated and compressed paroxetine admixed with dry excipients in the form of a tablet.

It should be appreciated that the term "dry" means substantially "dry" as opposed to the wholesale addition of water which was previously employed in the wet granulation process.

Direct compression techniques are generally known in the art of pharmaceutical science. For example, paroxetine is conventionally admixed with dry excipients and compressed into tablets.

Dry granulation techniques are generally also known in the art of pharmaceutical science. For example, paroxetine is conventionally admixed with dry excipients and compressed into large slugs or roller compacted into ribbon-like strands. The compacted material is then suitably milled to produce a free flowing powder which is then compressed into tablets.

Additional excipients may then be added and mixed with the free flowing powder before being compressed into tablets.

Examples of excipients include calcium phosphate, microcrystalline cellulose, sodium starch glycollate and magnesium stearate which may be admixed in appropriate ratios.

It should be appreciated that particularly good results are obtained when microcrystalline cellulose is absent from the formulation, this is surprising as tablets formulated in the absence of microcystalline cellulose are often prone to breaking up during manufacture or storage.

The paroxetine/excipient mixture may be compressed into an appropriate tablet shape. Preferred shapes include a pentagonal circumcircle, oval, round biconvex or a tilt-tablet such as those described in U.S. Pat. No. 4,493,822.

Paroxetine when incorporated into the above-mentioned tablets is suitably, present as the hydrochloride hemi-hydrate form which may be prepared according to the procedures outlined in U.S. Pat. No. 4,721,723.

The amount of paroxetine present in the above-mentioned tablets is in the range of 10 to 100 mg of paroxetine as measured in terms of the "free base". Particularly preferred amounts include 10 mg, 20 mg, 30 mg, 40 mg and 50 mg of paroxetine as measured in terms of the "free base". Particularly preferred amounts include 20 mg, 30 mg and 40 mg of paroxetine as measured in terms of the "free base".

Suitable procedures for preparing paroxetine include those mentioned in U.S. Pat. Nos. 4,009,196, 4,902,801, 4,861,893 and 5,039,803 and PCT/GB 93/00721.

It has been mentioned that paroxetine has particular utility in the treatment of depression, paroxetine may also be used in the treatment of mixed anxiety and depression, obsessive compulsive disorders, panic, pain, obesity, senile dementia, migraine, bulimia, anorexia, social phobia and the depression arising from premenstrual tension and adolescence.

The present invention therefore also provides a method of treating or preventing any of the above disorders which comprises administering an effective or prophylatic amount to a sufferer in need thereof of paroxetine which is formulated into a tablet using a process in which water is absent.

The present invention further provides a pharmaceutical composition comprising paroxetine which is formulated into a tablet using a process in which water is absent for use in treating or preventing of the above disorders.

The present invention further provides the use of paroxetine which is formulated into a tablet using a process in which water is absent in the manufacture of a medicament for treating or preventing the above disorders.

The following examples illustrate the present invention:

EXAMPLE 1

| INGREDIENTS | 20 mg Tablet | 30 mg Tablet |
|---|---|---|
| Paroxetine hydrochloride hemihydrate | 22.67 mg | 34.0 mg |
| Dicalcium Phosphate (DCP) | 83.34 mg | 125.0 mg |
| Microcrystalline Cellulose | 50.67 mg | 76.0 mg |
| Sodium Starch Glycollate | 8.34 mg | 12.5 mg |
| Magnesium Stearate | 1.67 mg | 2.5 mg |
| Tablet Weight | 166.7 mg | 250.0 mg |

Commercial source of the ingredients
Dicalcium Phosphate Dihydrate—Emcompress or Ditab*
Microcrystalline Cellulose—Avicel PH 102*
Sodium Starch Glycollate—Explotab.*
* Tradenames Method
1. Pass DCP through a screen and weigh it into a Planetary mixer.
2. Add 30 mesh Paroxetine to the bowl.
3. Add 20 mesh Avicel and Explotab and mix all the powders for 10 minutes.
4. Add magnesium Stearate and mix for 5 minutes.

Tablet into Pentagonal Tablets using the following punches:

| 30 mg Tablet | 9.5 mm | Circumcirle |
|---|---|---|
| 20 mg Tablet | 8.25 mm | Circumcircle |

The tablets are made satisfactorily on a single punch or a Rotary press.

EXAMPLE 2

| INGREDIENTS | 10 mg Tablet | 20 mg Tablet | 30 mg Tablet |
|---|---|---|---|
| Paroxetine hydrochloride hemihydrate | 11.40 mg | 22.80 mg | 34.20 mg |
| Sodium Starch Glycollate | 2.98 mg | 5.95 mg | 8.93 mg |
| Granular Dicalcium Phosphate (DITAB) or Dicafos | 158.88 mg | 317.75 mg | 476.63 mg |
| Magnesium Stearate | 1.75 mg | 3.50 mg | 5.25 mg |
| Tablet Weight | 175.00 mg | 350.00 mg | 525.00 mg |

Method
1. Paroxetine, Sodium Starch Glycollate and Dicalcium Phosphate Dihydrate are screened and mixed together in a suitable mixer. (Planetary, Cuble or High Energy Shear mixer.)
2. Add Magnesium Stearate and compress it into a tablet using a single punch or Rotary Tablet machine.

We claim:
1. A pharmaceutical composition in tablet form containing an amount of paroxetine selected from: 10 mg, 20 mg, 30 mg, 40 mg and 50 mg, wherein the amount of paroxetine is expressed as the free base, produced by a process which comprises the steps of:
   a) dry admixing paroxetine and excipients in a mixer to form a mixture; or
   b) dry admixing paroxetine and excipients, compressing the resulting combination into a slug material or roller compacting the resulting combination into a strand material, and milling the prepared material into a free flowing mixture; and
   c) compressing the mixture into tablets using a single punch or rotary tablet machine.

* * * * *

UNITED STATES PATENT AND TRADEMARK OFFICE
CERTIFICATE OF CORRECTION

PATENT : 6,113,944

DATED : September 5, 2000

INVENTOR(S) : Pathak, et al.

It is certified that error appears in the above-identified patent and that said Letters Patent is hereby corrected as shown below:

Delete Claim 1 and replace it with Claims 1 and 2 as follows.

Claim 1. A pharmaceutical composition in tablet form containing paroxetine, produced on a commercial scale by a process which comprises the steps of:
    a)     dry admixing paroxetine and excipients in a mixer to form a mixture; or
    b)     dry admixing paroxetine and excipients, compressing the resulting combination into a slug material or roller compacting the resulting combination into a strand material, and milling the prepared material into a free flowing mixture; and
    c)     compressing the mixture into tablets.

UNITED STATES PATENT AND TRADEMARK OFFICE
CERTIFICATE OF CORRECTION

PATENT : 6,113,944
DATED : September 5, 2000
INVENTOR(S) : Pathak, et al.

It is certified that error appears in the above-identified patent and that said Letters Patent is hereby corrected as shown below:

Claim 2. A pharmaceutical composition in tablet form according to claim 1 containing an amount of paroxetine selected from 10 mg, 20 mg, 30 mg, 40 mg and 50 mg, wherein the amount of paroxetine is expressed as the free base, produced on a commercial scale by a process which comprises the steps of:
    a)    dry admixing paroxetine and excipients in a mixer to form a mixture; or
    b)    dry admixing paroxetine and excipients, compressing the resulting combination into a slug material or roller compacting the resulting combination into a strand material, and milling the prepared material into a free flowing mixture; and
    c)    compressing the mixture into tablets using a single punch or rotary tablet machine.

Signed and Sealed this

Twenty-first Day of November, 2000

*Attest:*

Q. TODD DICKINSON

*Attesting Officer*    *Director of Patents and Trademarks*